United States Patent
Nishizaki et al.

(10) Patent No.: US 8,044,104 B2
(45) Date of Patent: Oct. 25, 2011

(54) PROSTAGLANDIN DERIVATIVE-CONTAINING AQUEOUS LIQUID PREPARATION

(75) Inventors: Kaori Nishizaki, Tokyo (JP); Takayuki Sato, Tokyo (JP); Kentaro Goto, Tokyo (JP); Kuniaki Ishii, Tokyo (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 12/666,804

(22) PCT Filed: May 28, 2008

(86) PCT No.: PCT/JP2008/059774
§ 371 (c)(1),
(2), (4) Date: Dec. 26, 2009

(87) PCT Pub. No.: WO2009/004873
PCT Pub. Date: Jan. 8, 2009

(65) Prior Publication Data
US 2010/0204331 A1    Aug. 12, 2010

(30) Foreign Application Priority Data
Jun. 29, 2007 (JP) ................................. 2007-172331

(51) Int. Cl.
*A01N 29/02* (2006.01)
*A01N 31/04* (2006.01)
*A61K 31/08* (2006.01)

(52) U.S. Cl. .................... 514/758; 514/723; 514/738

(58) Field of Classification Search .................... None
See application file for complete search history.

(56) References Cited

U.S. PATENT DOCUMENTS

| | | |
|---|---|---|
| 2002/0146439 A1 | 10/2002 | DeLong et al. |
| 2005/0009917 A1 | 1/2005 | Sato et al. |
| 2005/0152721 A1 | 7/2005 | Kikuchi et al. |
| 2005/0192357 A1* | 9/2005 | Arai et al. ............... 514/573 |
| 2006/0121069 A1 | 6/2006 | DeLong et al. |

FOREIGN PATENT DOCUMENTS

| | | |
|---|---|---|
| EP | 0470251 A1 | 2/1992 |
| EP | 0896816 A1 | 2/1999 |
| EP | 1852120 A1 * | 11/2007 |
| JP | 2-282329 A | 11/1990 |
| JP | 05-229928 A | 9/1993 |
| JP | 2000-319163 A | 11/2000 |
| JP | 2003-238328 A | 8/2003 |
| JP | 2003-238336 A | 8/2003 |
| JP | 2003-528895 A | 9/2003 |
| JP | 2005-247842 A | 9/2005 |
| WO | 97/30696 A1 | 8/1997 |
| WO | 2004/014394 A1 | 2/2004 |
| WO | 2005/044276 A1 | 5/2005 |
| WO | 2006/085655 A1 | 8/2006 |

OTHER PUBLICATIONS

Vippagunta et al., Advanced Drug Delivery Reviews, 48, pp. 3-26, (2001).*
International Search Report dated Aug. 19, 2008, issued in International Application No. PCT/JP2008/059774.

* cited by examiner

*Primary Examiner* — Sreeni Padmanabhan
*Assistant Examiner* — Svetlana M Ivanova
(74) *Attorney, Agent, or Firm* — Sughrue Mion, PLLC

(57) ABSTRACT

Provided is an aqueous liquid preparation comprising: (a) any one of a prostaglandin derivative being represented by the following formula (I), a pharmaceutically acceptable salt thereof and a hydrate thereof; and (b) at least one polyol of glycerin, propylene glycol, dipropylene glycol and 1,3-butylene glycol.

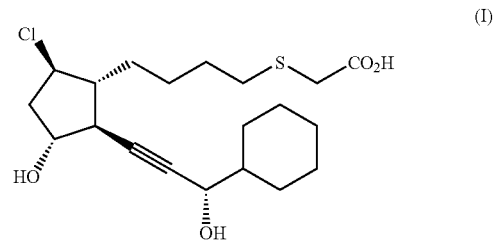

(I)

3 Claims, 1 Drawing Sheet

PROSTAGLANDIN DERIVATIVE-CONTAINING AQUEOUS LIQUID PREPARATION

This application is a National Stage of International Application No. PCT/JP2008/059774, filed May 28, 2008, claiming priority based on Japanese Application No. 2007-172331, Jun. 29, 2007, the contents of all of which are incorporated herein by reference in their entirety.

TECHNICAL FIELD

The present invention relates to an aqueous liquid preparation containing a prostaglandin derivative, and mainly relates to a lotion preparation containing a prostaglandin derivative.

BACKGROUND OF THE INVENTION

Some prostaglandin derivatives are known to have antipruritic effects, and there is disclosed the use of such prostaglandin derivatives as prophylactic or therapeutic external preparations for diseases such as atopic dermatitis and scabies (refer to Patent Document 1). For example, disclosed is a prophylactic or therapeutic agent, for pruritic symptoms, containing a prostaglandin derivative represented by the following formula (I):

[Chemical Formula 1]

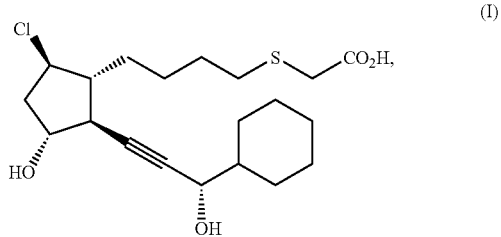

(I)

a pharmaceutically acceptable salt thereof, or a hydrate thereof (hereinafter, referred to as a "compound of formula I") as an active ingredient.

Such a prophylactic or therapeutic agent, for atopic dermatitis or the like, containing the compound of formula I as an active ingredient is provided as an external preparation such as an ointment preparation or a lotion preparation (refer to Patent Document 1).

However, it is known that the compound of formula I is scarcely soluble in water and that the storage stability of the compound of formula I is significantly deteriorated when the compound of formula I is in a water-dispersed state or the like (refer to Patent Document 2).

Accordingly, in order to provide an aqueous external preparation, such as a lotion preparation, containing the compound of formula I, a technique has been demanded which allows the compound of formula I to uniformly dissolve in an aqueous external preparation and thereby ensures the storage stability of the compound of formula I.

Patent Document 1: International Publication No. WO2004/014394

Patent Document 2: International Publication No. WO2006/085655

DISCLOSURE OF THE INVENTION

Problem to be Solved by the Invention

The compound of formula I dissolved in ethanol, whereby it is possible to ensure the storage stability of the compound of formula I. However, because of its skin-irritating properties, ethanol is not preferable as a solvent for therapeutic external preparations for atopic dermatitis, scabies, and the like. Meanwhile, the stability of the compound of formula I is deteriorated when a surfactant such as polyethylene glycol or polysorbate 80 is used as a solubilizer to improve the solubility of the compound of formula I in water. Moreover, it has been found out that, the blending of an anti-oxidant such as butylhydroxytoluene (BHT) or a chelating agent such as EDTA does not contribute to the improvement of the storage stability of the compound of formula I, or rather reduces the storage stability thereof.

Accordingly, an object of the present invention is to provide an aqueous liquid preparation in which the compound of formula I is uniformly dissolved and the storage stability thereof is ensured.

Means for Solving the Problems

The present inventors have earnestly studied in order to resolve the problems described above. As a result, the inventors have found that, in an aqueous solution containing a certain kind of polyol at a certain proportion as a solubilizer, the compound of formula I is dissolved at a relatively high concentration, and the storage stability thereof is also ensured.

An aspect according to the present invention based on the above-described findings is an aqueous liquid preparation comprising: (a) any one of a prostaglandin derivative being represented by the following formula (I):

[Chemical formula 2]

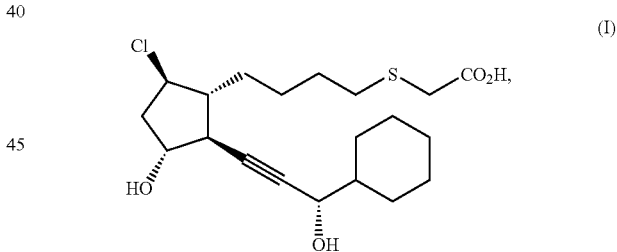

(I)

a pharmaceutically acceptable salt thereof and a hydrate thereof; and (b) at least one polyol of glycerin, propylene glycol, dipropylene glycol and 1,3-butylene glycol.

EFFECT OF THE INVENTION

According to the present invention, it is possible to provide a prostaglandin-containing aqueous liquid preparation in which the compound of formula I is uniformly dissolved, and the storage stability thereof is ensured.

DETAILED DESCRIPTION OF THE PREFERRED EMBODIMENTS

The compound of formula I in the present invention has an excellent therapeutic effect for pruritic symptoms. For example, the compound of formula I can be used for an antipruritic agent to itching caused by atopic dermatitis. A method for producing this antipruritic agent is described in WO2004/014394 (refer to Patent Document 1).

The solubility of the compound of formula I in water at 25° C. is approximately 0.06 mg/mL.

A content (blended amount) of the compound of formula I is from 0.0001 to 0.02 (w/v %), and preferably from 0.001 to 0.02 (w/v %), of the total of the aqueous liquid preparation. A content less than 0.0001 (w/v %) is not preferable because the content of the compound of formula I is so small that antipruritic effects are less likely to be exhibited sufficiently. Meanwhile, a content exceeding 0.02 (w/v %) is not preferable because such a content makes it difficult to ensure the solubility of the compound of formula I.

Examples of the "polyol" include glycerin, propylene glycol, dipropylene glycol, and 1,3-butylene glycol. 1,3-butylene glycol is preferable because 1,3-butylene glycol provides an excellent storage stability of the compound of formula I, and exhibits moderate skin irritation.

A content (blended amount) of the polyol is from 30 to 80 (w/v %), and preferably from 40 to 80 (w/v %), of the total of the aqueous liquid preparation. The content of the polyol in the aqueous liquid preparation less than 30 (w/v %) is not preferable, because the compound of formula I does not dissolve (at 5° C.) in the aqueous liquid preparation in a case where the concentration of the compound of formula I in the aqueous liquid preparation exceeds 0.01 (w/v %), and because the stability of the compound of formula I is significantly deteriorated in a case where the concentration of the compound of formula I in the aqueous liquid preparation is 0.01 (w/v %) or less. Meanwhile, the content of the polyol in the aqueous liquid preparation exceeding 80 (w/v %) is not preferable, because, regardless of the concentration of the compound of formula I in the aqueous liquid preparation, the stability of the compound of formula I in the aqueous liquid preparation significantly deteriorates.

Note that an aqueous liquid preparation of the compound of formula I containing 1,3-butylene glycol at a concentration of 30 (w/v %) or more is found to have a sufficient preservatives-effectiveness in a preservatives-effectiveness test, and hence has a merit of being providable as an external preparation without blending a preservative (refer to Test Example 4).

The aqueous liquid preparation of the present invention is provided mainly as an aqueous external liquid preparation which contains the compound of formula I and which is effective in therapy or the like for pruritic symptoms such as atopic dermatitis. The most preferable form is a lotion preparation.

A pH of the aqueous liquid preparation of the present invention is normally 4 to 9, because of the following reason. Specifically, a pH less than 4 is too low as compared to the pH of the skin, and a pH exceeding 9 is too high as compared to the pH of the skin. As a result, both cases may involve occurrence of skin irritation, and thus are not preferable.

Moreover, by making the pH of the aqueous liquid preparation of the present invention between 4 and 7, the stability of the compound of formula I is improved. Specifically, when the pH is less than 4, or when the pH exceeds 7, analogues of the compound of formula I are formed, thereby reducing the stability of the compound of formula I.

For these reasons, a more preferable range of pH of the present invention is from 4 to 7, in view of skin irritation and stability.

The aqueous liquid preparation of the present invention is prepared by dissolving the compound of formula I in the polyol such as 1,3-butylene glycol and adding water thereto followed by stirring and mixing.

To the aqueous liquid preparation of the present invention, in addition to the compound of formula I and the polyol such as 1,3-butylene glycol, a pH adjustor, a solubilizer other than the polyol, an antioxidant, a surfactant, a preservative, a humectant, a thickener, a flavor, a dye or the like can be blended, if necessary, as long as the effect of the present invention is not impaired.

EXAMPLES

The present invention is described in further detail below by showing Examples, Comparative Examples and Test Examples.

Note that, as a high-performance liquid chromatography system, a LC10VP series manufactured by SHIMADZU CORPORATION was used, and the tests were conducted under the following measurement conditions.

Meanwhile, as a pH measuring instrument, a HM-50G or a HM-50V manufactured by DKK-TOA CORPORATION was used.

Column: Develosil ODS-HG-5 (Inner diameter: 4.6 mm, Length: 15 cm, manufactured by Nomura Chemical Co., Ltd.)

Column temperature: 40° C.

(Assay of Compound of Formula I)

Mobile phase: mixed solution of water/acetonitrile/phosphoric acid (610:390:1)

Flow rate: approximately 0.9 mL/min

Detection wavelength: 200 nm

Example 1

To 30 g of propylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 2

To 45 g of propylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 3

To 30 g of glycerin, 0.01 g of the compound of formula I was added, and mixed by stirring. After dissolution, water was added to bring the total amount to 100 mL, followed by uniform mixing. A lotion preparation with the concentration of the compound of formula I being 0.01 (w/v %) was obtained.

Example 4

To 45 g of glycerin, 0.01 g of the compound of formula I was added, and mixed by stirring. After dissolution, water was added to bring the total amount to 100 mL, followed by uniform mixing. A lotion preparation with the concentration of the compound of formula I being 0.01 (w/v %) was obtained.

Example 5

To 30 g of dipropylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 6

To 30 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 7

To 45 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 8

To 30 g of propylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 9

To 45 g of propylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 10

To 30 g of glycerin, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 11

To 45 g of glycerin, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 12

To 30 g of dipropylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 13

To 30 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 14

To 45 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 15

To 40 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 16

To 50 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 17

To 60 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 18

To 80 g of 1,3-butylene glycol, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Example 19

To 40 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 20

To 50 g of 1,3-butylene glycol, 0.0001 g of the compound of formula I was added, and mixed by stirring. After dissolu-

Example 21

To 60 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 22

To 80 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Example 23

To 45 g of 1,3-butylene glycol, 0.001 g of the compound of formula I was added, and mixed by stirring. After dissolution, water was added to bring the total amount to 100 mL, followed by uniform mixing. A lotion preparation with the concentration of the compound of formula I being 0.001 (w/v %) was obtained.

Example 24

To 45 g of 1,3-butylene glycol, 0.005 g of the compound of formula I was added, and mixed by stirring. After dissolution, water was added to bring the total amount to 100 mL, followed by uniform mixing. A lotion preparation with the concentration of the compound of formula I being 0.005 (w/v %) was obtained.

Example 25

To 45 g of 1,3-butylene glycol, 0.01 g of the compound of formula I was added, and mixed by stirring. After dissolution, water was added to bring the total amount to 100 mL, followed by uniform mixing. A lotion preparation with the concentration of the compound of formula I being 0.01 (w/v %) was obtained.

Example 26

To 30 g of 1,3-butylene glycol, 0.01 g of the compound of formula I was added, and mixed by stirring. After dissolution, water was added to bring the total amount to 100 mL, followed by uniform mixing. A lotion preparation with the concentration of the compound of formula I being 0.01 (w/v %) was obtained.

Comparative Example 1

To 30 g of polyethylene glycol 400, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Comparative Example 2

To 45 g of polyethylene glycol 400, 0.02 g of the compound of formula I was added, and mixed by stirring. After dissolution, water was added to bring the total amount to 100 mL, followed by uniform mixing. A lotion preparation with the concentration of the compound of formula I being 0.02 (w/v %) was obtained.

Comparative Example 3

To 5 g of polysorbate 80, 0.02 g of the compound of formula I was added, and mixed by stirring. After dissolution by heating, water was added to bring the total amount to 100 mL, followed by uniform mixing. A lotion preparation with the concentration of the compound of formula I being 0.02 (w/v %) was obtained.

Comparative Example 4

To 10 g of polysorbate 80, 0.02 g of the compound of formula I was added, and mixed by stirring. After dissolution by heating, water was added to bring the total amount to 100 mL, followed by uniform mixing. A lotion preparation with the concentration of the compound of formula I being 0.02 (w/v %) was obtained.

Comparative Example 5

To 20 g of ethanol, 0.01 g of the compound of formula I was added, and mixed by stirring. After dissolution, water was added to bring the total amount to 100 mL, followed by uniform mixing. A lotion preparation with the concentration of the compound of formula I being 0.01 (w/v %) was obtained.

Comparative Example 6

To 30 g of polyethylene glycol 400, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 7

To 45 g of polyethylene glycol 400, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 8

To 5 g of polysorbate 80, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 9

To 1,3-butylene glycol, 0.02 g of the compound of formula I was added, and mixed by stirring. After dissolution, 1,3-butylene glycol was added to bring the total amount to 100 mL, followed by uniform mixing. A lotion preparation with the concentration of the compound of formula I being 0.02 (w/v %) was obtained.

Comparative Example 10

To 5 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 11

To 20 g of 1,3-butylene glycol, 0.0001 g of the compound of formula I was added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 12

To 1,3-butylene glycol, 0.0001 g of the compound of formula I was added, and mixed by stirring. After dissolution, 1,3-butylene glycol was added to bring the total amount to 100 mL, followed by uniform mixing. A lotion preparation with the concentration of the compound of formula I being 0.0001 (w/v %) was obtained.

Comparative Example 13

To 45 g of 1,3-butylene glycol, 0.1 g of butylhydroxytoluene and 0.01 g of the compound of formula I were added, and mixed by stirring. After dissolution, water was added to bring the total amount to 100 mL, followed by uniform mixing. A lotion preparation with the concentration of the compound of formula I being 0.01 (w/v %) was obtained.

Comparative Example 14

To 45 g of 1,3-butylene glycol, 0.1 g of disodium EDTA and 0.01 g of the compound of formula I were added, and mixed by stirring. After dissolution, water was added to bring the total amount to 100 mL, followed by uniform mixing. A lotion preparation with the concentration of the compound of formula I being 0.01 (w/v %) was obtained.

Comparative Example 15

To 45 g of 1,3-butylene glycol, 0.1 g of butylhydroxytoluene and 0.0001 g of the compound of formula I were added, and mixed by stirring. After dissolution, water was added to bring the total amount to 100 mL, followed by uniform mixing. A lotion preparation with the concentration of the compound of formula I being 0.0001 (w/v %) was obtained.

Comparative Example 16

To 45 g of 1,3-butylene glycol, 0.1 g of the compound of formula I was added, and mixed by stirring. After dissolution, water was added to bring the total amount to 100 mL, followed by uniform mixing. A lotion preparation with the concentration of the compound of formula I being 0.1 (w/v %) was obtained.

Test Example 1

Stability of the compound of formula I in various solutions was examined. As additives, polyols (propylene glycol, glycerin, dipropylene glycol (DPG), 1,3-butylene glycol, and polyethylene glycol 400), a surfactant (polysorbate 80) and an alcohol (ethanol) were selected. As shown in Examples 1 to 7 and Comparative Examples 1 to 5, the lotion preparations with 0.01 (w/v %) or 0.02 (w/v %) of the compound of formula I were each prepared, depending on the solubility, by adding 30 (w/v %) or 45 (w/v %) of one of propylene glycol, glycerin, dipropylene glycol (DPG), 1,3-butylene glycol and polyethylene glycol 400, 5 (w/v %) or 10 (w/v %) of polysorbate 80, or 20 (w/v %) of ethanol. These were filled into glass tubes. The compound of formula I after each of two-week storage and four-week storage at 50° C. was assayed by a high-performance liquid chromatography. The respective residual ratios of the compound of formula I were calculated to evaluate the storage stability at 50° C. Table 1 shows the results.

TABLE 1

|  |  | Type of additive | | | | | | | |
| --- | --- | --- | --- | --- | --- | --- | --- | --- | --- |
|  |  | Propylene glycol | | Glycerin | | DPG (*1) | | 1,3-butylene glycol | |
| Concentration of additive (w/v %) | | 30 | 45 | 30 | 45 | 30 | 30 | 45 | 45 |
| Concentration of compound of formula I (w/v %) | | 0.02 | 0.02 | 0.01 | 0.01 | 0.02 | 0.02 | 0.02 | 0.01 |

|  |  | Recipe | | | | | | | |
| --- | --- | --- | --- | --- | --- | --- | --- | --- | --- |
|  |  | Example 1 | Example 2 | Example 3 | Example 4 | Example 5 | Example 6 | Example 7 | Example 25 |
| Residual ratio of compound of formula I (%) | At time of start | 100.0 | 100.0 | 100.0 | 100.0 | 100.0 | 100.0 | 100.0 | 100.0 |
|  | After two weeks at 50° C. | 94.0 | 96.6 | 85.3 | 79.9 | 92.5 | 96.5 | 99.1 | 96.7 |
|  | After four weeks at 50° C. | 83.9 | 92.4 | 72.6 | 70.6 | 91.8 | 87.2 | 97.6 | 93.0 |

TABLE 1-continued

| | | Type of additive | | | | | | |
|---|---|---|---|---|---|---|---|---|
| | | Polyethylene glycol 400 | | Polysorbate 80 | | Ethanol | 1,3-butylene glycol/BHT (*2) | 1,3-butylene glycol/ EDTA |
| Concentration of additive (w/v %) | | 30 | 45 | 5 | 10 | 20 | 45/0.1 | 45/0.1 |
| Concentration of compound of formula I (w/v %) | | 0.02 | 0.02 | 0.01 | 0.01 | 0.01 | 0.01 | 0.01 |
| | | Recipe | | | | | | |
| | | Comparative Example 1 | Comparative Example 2 | Comparative Example 3 | Comparative Example 4 | Comparative Example 5 | Comparative Example 13 | Comparative Example 14 |
| Residual ratio of compound of formula I (%) | At time of start | 100.0 | 100.0 | 100.0 | 100.0 | 100.0 | 100.0 | 100.0 |
| | After two weeks at 50° C. | 0.0 | 0.0 | 0.0 | 0.0 | 95.9 | 96.5 | 84.8 |
| | After four weeks at 50° C. | 0.0 | 0.0 | 0.0 | 0.0 | 91.5 | — | — |

(*1) DPG: Dipropylene glycol
(*2) BHT: Butylhydroxytoluene

According to Table 1, the storage stability of the compound of formula I greatly differed depending on the kinds of the additives used. In each of Comparative Examples 1 to 4, where polyethylene glycol 400 or polysorbate 80 was blended, the residual ratio after two-week storage at 50° C. was 0%, so the compound of formula I was unstable. In contrast, in each of Examples 1 to 7, where propylene glycol, glycerin, dipropylene glycol (DPG) or 1,3-butylene glycol was blended, and in Comparative Example 5, where ethanol was blended, the residual ratio under the same conditions was approximately 80% or more, so the compound of formula I was stable. In consideration of the skin irritation due to ethanol, additives suitable for stabilizing the compound of formula I are glycerin, propylene glycol, dipropylene glycol and 1,3-butylene glycol. Meanwhile, in Comparative Example 13 where butylhydroxytoluene (BHT), which is an anti-oxidant, was blended, and in Comparative Example 14 where EDTA, which is a chelating agent, was blended, improvement in stability was not observed, or rather the stability was deteriorated, in comparison with Example 25, where none of them was blended.

Test Example 2

In terms of relationship of the additives shown in Test Example 1 with the storage stability of the compound of formula I, similar examination to that in Test Example 1 was conducted on the lotion preparations with 0.0001 (w/v %) of the compound of formula I, to evaluate the storage stability at 50° C. Table 2 shows the results.

TABLE 2

| | | Type of additive | | | | | | |
|---|---|---|---|---|---|---|---|---|
| | | Propylene glycol | | Glycerin | | DPG (*1) | 1,3-butylene glycol | |
| Concentration of additive (w/v %) | | 30 | 45 | 30 | 45 | 30 | 30 | 45 |
| Concentration of compound of formula I (w/v %) | | 0.0001 | 0.0001 | 0.0001 | 0.0001 | 0.0001 | 0.0001 | 0.0001 |
| | | Recipe | | | | | | |
| | | Example 8 | Example 9 | Example 10 | Example 11 | Example 12 | Example 13 | Example 14 |
| Residual ratio of compound of formula I (%) | At time of start | 100.0 | 100.0 | 100.0 | 100.0 | 100.0 | 100.0 | 100.0 |
| | After two weeks at 50° C. | 96.7 | — | 93.4 | 90.9 | 92.2 | 87.6 | 93.2 |
| | After four weeks at 50° C. | — | 92.9 | 83.9 | 90.8 | — | 91.5 | 93.3 |

TABLE 2-continued

|  |  | Type of additive | | | |
|---|---|---|---|---|---|
|  |  | Polyethylene glycol 400 | Polysorbate 80 | 1,3-butylene glycol/ BHT (*2) | |
| Concentration of additive (w/v %) | | 30 | 45 | 5 | 45/0.1 |
| Concentration of compound of formula I (w/v %) | | 0.0001 | 0.0001 | 0.0001 | 0.0001 |
|  |  | Recipe | | | |
|  |  | Comparative Example 6 | Comparative Example 7 | Comparative Example 8 | Comparative Example 15 |
| Residual ratio of compound of formula I (%) | At time of start | 100.0 | 100.0 | 100.0 | 100.0 |
| | After two weeks at 50° C. | 6.9 | 0.0 | 0.0 | 92.5 |
| | After four weeks at 50° C. | — | — | — | 70.5 |

(*1) DPG: Dipropylene glycol
(*2) BHT: Butylhydroxytoluene

According to Table 2, in each of Comparative Examples 6 to 8, where polyethylene glycol 400 or polysorbate 80 was blended, the stability of the compound of formula I was low, whereas, in each of Example 8 to 14, where propylene glycol, glycerin, dipropylene glycol (DPG) or 1,3-butylene glycol was blended, the stability was high. These showed the same trend as in the cases of the lotion preparations in Test Example 1, where the concentration of the compound of formula I was 0.01 (w/v %) or 0.02 (w/v %). Meanwhile, in Comparative Example 15, where butylhydroxytoluene (BHT), which is an anti-oxidant, was added, an improvement effect on the stability was not observed, or rather the stability was deteriorated, in comparison with Example 14, where no butylhydroxytoluene (BHT) was added.

Test Example 3

Solutions with the concentration of the compound of formula I being 0.02 (w/v %) were attempted to be prepared, with the concentrations of 1,3-butylene glycol being 5, 20, 30, 40, 45, 50, 60, 80 and 100 (w/v %). However, at 5 (w/v %) and 20 (w/v %), the compound of formula I was not dissolved. For this reason, the quantitative values of the compound of formula I stored at 50° C. with the concentrations of 1,3-butylene glycol being 30, 40, 45, 50, 60, 80 and 100 (w/v %) were assayed by liquid chromatography, to evaluate the stability. FIG. 1 shows the results.

As described above, when the concentration of 1,3-butylene glycol was less than 30 (w/v %), the compound of formula I was not sufficiently dissolved. Meanwhile, in the solution with the concentration of 1,3-butylene glycol being 100 (w/v %), the stability of the compound of formula I was extremely low. In contrast, in solutions with the concentrations of 1,3-butylene glycol being 30 to 80 (w/v %), the residual ratios of the compound of formula I after two-week storage at 50° C. were approximately 95% or more. In particular, within the range where the concentration of 1,3-butylene glycol was from 40 to 80 (w/v %), the compound of formula I was so stable that the residual ratios were kept at 90 (w/v %) or more even after four-week storage at 50° C.

From the results described above, it was found out that, in 1,3-butylene glycol solutions within the range of concentration from 30 to 80 (w/v %), the stability of the compound of formula I was particularly high.

Test Example 4

Similar examination to that in Test Example 3 was performed on solutions of 0.0001 (w/v %) of the compound of formula I, with the concentrations of 1,3-butylene glycol being 5 to 100 (w/v %). FIG. 2 shows the results. According to FIG. 2, the residual ratios of the compound of formula I after two-week storage at 50° C. in solutions with the concentrations of 1,3-butylene glycol being 30 to 80 (w/v %) were as high as approximately 85% or more. In particular, within the range where the concentration of 1,3-butylene glycol was 40 to 80 (w/v %), the stability was high. In contrast, with a concentration of 1,3-butylene glycol being less than 30 (w/v %) or more than 80 (w/v %), the stability of the compound of formula I was lowered.

Accordingly, it was found out that, to dissolve stably the compound of formula I, it was necessary to set the concentration of 1,3-butylene glycol within the range of 30 to 80 (w/v %).

Test Example 5

The lotion preparations of Examples 7, 14, 23 and 25 were respectively filled into glass tubes. The storage stability of the lotion preparations, using 1,3-butylene glycol as a solubilizer and respectively containing a compound of formula I of 0.0001 (w/v %), 0.001 (w/v %), 0.01 (w/v %) and 0.02 (w/v %) was checked under various temperature conditions. Table 3 shows the results.

TABLE 3

|  |  | Concentration of compound of formula I (w/v %) | | | |
|---|---|---|---|---|---|
|  |  | 0.0001 | 0.001 | 0.01 | 0.02 |
|  |  | Recipe | | | |
|  |  | Example 14 | Example 23 | Example 25 | Example 7 |
| Residual ratio of | At time of start | 100.0 | 100.0 | 100.0 | 100.0 |

TABLE 3-continued

| | | Concentration of compound of formula I (w/v %) | | | |
|---|---|---|---|---|---|
| | | 0.0001 | 0.001 | 0.01 | 0.02 |
| | | | Recipe | | |
| | | Example 14 | Example 23 | Example 25 | Example 7 |
| compound of formula I (%) | After one month at 25° C. | 96.0 | — | 98.5 | 102.5 |
| | After three months at 25° C. | 98.9 | 100.8 | 98.5 | — |
| | After three months at 5° C. | 101.6 | 99.5 | 99.5 | 100.1 |
| | After six months at 5° C. | — | — | 95.1 | 100.3 |

According to Table 3, it was found out that each of the lotion preparations with the concentration of the compound of formula I being from 0.0001 (w/v %) to 0.02 (w/v %) was stable at 25° C. and 5° C.

Test Example 6

Preservatives-effectiveness test was performed on the lotion preparations of Examples 25 and 26, in accordance with "Preservatives-Effectiveness Tests" in General Information of The Japanese Pharmacopoeia Fourteenth Edition. The preservatives-effectiveness test is a method of evaluating microbiologically a product itself packaged in a multidose container or the efficacy of preservatives added to the product. The preservatives-effectiveness is evaluated by forced inoculation and mixing of the test strains in the product, and follow-up of the survivals of the test strains with time. As test strains, three kinds of bacteria: *Escherichia coli* IFO 3972 (ATCC 8739); *Pseudomonas aeruginosa* IFO 13275 (ATCC 9027); and *Staphylococcus aureus* IFO 13276 (ATCC 6538), one kind of yeast: *Candida albicans* IFO 1594 (ATCC 10231), and one kind of fungi: *Aspergillus niger* IFO 9455 (ATCC 16404) were used. A liquid of test cells prepared by using these strains was inoculated into the lotion preparations. After the lotion preparations were stored at 20 to 25° C. for 28 days, the numbers of viable cells were determined. As a result, the numbers of cells after 14-days storage were less than 1% of their respective corresponding numbers of viable cells at the start of the test. In addition, the numbers of fungi after 14-days storage and 28-days storage remained at the same level as the number of viable cells at the start of the test or at a lower level. Accordingly, in both cases, preservatives-effectiveness was observed, and it was confirmed that the lotion preparations of the compound of formula I with the concentration of 1,3-butylene glycol being 30 (w/v %) or more did not require addition of a preservative.

Test Example 7

In order to evaluate the skin irritation of the lotion preparations of Example 25, where the concentration of the compound of formula I was 0.01 (w/v %), and Comparative Example 16, where the concentration of the compound of formula I was 0.1 (w/v %), 0.1 mL of one of the lotion preparations of Example 25 and Comparative Example 16 and an aqueous solution (base) of 45 (w/v %) of 1,3-butylene glycol was continuously applied once a day for 28 days to healthy and damaged shaved back skins (2.5×2.5 cm), which were not covered, of each 4-month-old male Japanese albino rabbit. In accordance with the Draize scale (Draize: "Appraisal of the safety of chemicals in foods, drugs and cosmetics", P. 46-59, Association of Food & Drug Officials of the United States, TX, 1959), the cumulative irritancy was evaluated. Table 4 shows the results.

TABLE 4

| | | | | | Mean score (MTS)* | |
|---|---|---|---|---|---|---|
| Concentration of compound of formula I (w/v %) | Administered sample | Number of examples | Skin condition | Skin reaction | Average value during application period | Total average value |
| 0 | Aqueous solution with 45% of 1,3-butylene glycol | 6 | Healthy | Erythema and eschar | 0.06 | 0.06 |
| | | | | Edema | 0 | |
| | | | | Total | 0.06 | |
| | | | Damaged | Erythema and eschar | 0.06 | |
| | | | | Edema | 0 | |
| | | | | Total | 0.06 | |
| 0.01 | Example 25 | 6 | Healthy | Erythema and eschar | 0.04 | 0.04 |
| | | | | Edema | 0 | |
| | | | | Total | 0.04 | |
| | | | Damaged | Erythema and eschar | 0.04 | |
| | | | | Edema | 0 | |
| | | | | Total | 0.04 | |

TABLE 4-continued

| Concentration of compound of formula I (w/v %) | Administered sample | Number of examples | Skin condition | Skin reaction | Mean score (MTS)* Average value during application period | Total average value |
|---|---|---|---|---|---|---|
| 0.1 | Comparative Example 16 | 6 | Healthy | Erythema and eschar | 0.12 | 0.12 |
| | | | | Edema | 0 | |
| | | | Damaged | Total Erythema and eschar | 0.12 0.11 | |
| | | | | Edema | 0 | |
| | | | | Total | 0.11 | |

*MTS 2 or less: weak irritant, 2 to 5: moderate irritant, 5 to 8: strong irritant MTS 2 or less: weak irritant, 2 to 5: moderate irritant, 5 to 8: strong irritant.

According to naked-eye observation, very slight erythema was sporadically observed in some of the animals during the administration period. However, according to Table 4, each mean score (MTS) thereof was 2 or less, and hence evaluation "weak irritant" was made in accordance with the scale.

Moreover, a single-dose of 0.1 mL of the lotion preparation prepared in Example 25 or Comparative Example 16 was administered as eye drops into the conjunctival sac of each similar male Japanese albino rabbit. Then, evaluation was made in accordance with the eye irritation scales of Draize as well as Kay and Calandra (Kay and Calandra: "Interpretation of eye irritation tests" J. Soc. Cosm. Chem., 13, p 281-289, 1962.). Table 5 shows the results.

According to Table 5, the mean score (MTS) in the case where the aqueous solution with 70% of ethanol was administered reached 37.8 at its maximum value. According to the evaluation scale, ethanol was evaluated to be "moderately irritant." Meanwhile, in Comparative Example 16, iris congestion and increase in conjunctival discharge were observed for a short period of time, and hence Comparative Example 16 was evaluated as "very slightly irritant". In contrast, in Example 25, no irritation was observed throughout the observation period, and hence Example 25 was evaluated as "non-irritant."

From the results described above, the lotion preparation of Example 25, where the concentration of the compound of formula I was 0.01 (w/v %), was evaluated to have weak irritancy, or no irritancy to the damaged skin or to the eyes, and Comparative Example 16, where the concentration of the compound of formula I was 0.1 (w/v %), which was higher than that in Example 25, was evaluated as weakly irritant, or very slightly irritant.

Test Example 8

To evaluate the drug efficacy of the lotion preparations prepared in Examples 14, 23 and 25, the effect on spontaneous scratching behaviors was examined in male 23-week old NC/Nga mice. In accordance with the document (Takano N et al.: European Journal of Pharmacology, 471 (2003) 223-8), 0.25 mL of one of the lotion preparations prepared in Examples 14, 23 and 25 and an aqueous solution with 45 (w/v %) of 1,3-butylene glycol was applied by spraying, to each mouse whose back was shaved on the day before the administration. The number of scratching behaviors was measured by detecting the movement of a magnet embedded in the hind limb by use of a coil. Table 6 shows the results.

TABLE 5

| Concentration of compound of formula I (w/v %) | Administered sample | Number of examples | Mean score (MTS)* Time elapsed after administration (time) | | | | | | | Maximum value* |
|---|---|---|---|---|---|---|---|---|---|---|
| | | | 1 | 3 | 6 | 24 | 48 | 72 | 168 | |
| — | 70% of ethanol | 6 | 37.8 | 30.8 | 25.7 | 23.2 | 16.3 | 11.5 | 3.3 | 37.8 |
| 0.01 | Example 25 | 6 | 0.0 | 0.0 | 0.0 | 0.0 | 0.0 | 0.0 | 0.0 | 0.0 |
| 0.1 | Comparative Example 16 | 6 | 0.0 | 4.5 | 4.2 | 0.8 | 0.0 | 0.0 | 0.0 | 4.5 |

*Maximum value of MTS 0 to 0.5: non-irritant, 0.5 to 2.5: virtually non-irritant, 2.5 to 15: very slightly irritant, 15 to 25: slightly irritant, 25 to 50: moderately irritant
*Maximum value of MTS 0 to 0.5: non-irritant, 0.5 to 2.5: virtually non-irritant, 2.5 to 15: very slightly irritant, 15 to 25: slightly irritant, 25 to 50: moderately irritant

TABLE 6

| Concentration of compound of formula I (w/v %) | Administered sample | Rate of change of scratching behavior (%) |
|---|---|---|
| 0% | Aqueous solution with 45% of 1,3-butylene glycol | 98.4 ± 8.3 |
| 0.0001% | Example 14 | 88.7 ± 8.6 |

TABLE 6-continued

| Concentration of compound of formula I (w/v %) | Administered sample | Rate of change of scratching behavior (%) |
| --- | --- | --- |
| 0.001% | Example 23 | 73.2 ± 4.7 * |
| 0.01% | Example 25 | 70.3 ± 6.7 * |

* significant difference was observed as compared to aqueous solution with 45% of 1,3-butylene glycol According to Table 6, in comparison with the number of scratching bouts within 24 hours before the application of the administered sample, the scratching behavior in the group to which the aqueous solution (base) with 45 (w/v %) of 1,3-butylene glycol was administered was not influenced, whereas, in the groups to which the lotion preparation containing the compound of formula I was administered, the value of the number of the scratching bouts became smaller with increase in concentration of the drug. In each of the groups with the concentration of the compound of formula I being 0.001 (w/v %) or 0.01 (w/v %), a more significant effect of decreasing the scratching behavior was observed, than in the group to which the aqueous solution with 45 (w/v %) of 1,3-butylene glycol was administered.

Accordingly, it was confirmed that the lotion preparations containing the compound of formula I according to the present invention had an improved solubility, an improved stability of the compound of formula I, preservatives-effectiveness and no skin irritation, and exhibited a sufficient drug efficacy.

INDUSTRIAL APPLICABILITY

According to the present invention, it is possible to provide an external preparation, such as a lotion preparation, containing the prostaglandin derivative represented by formula I as an active ingredient, and being prophylactically and therapeutically effective for pruritic symptoms such as atopic dermatitis.

Figure 1:
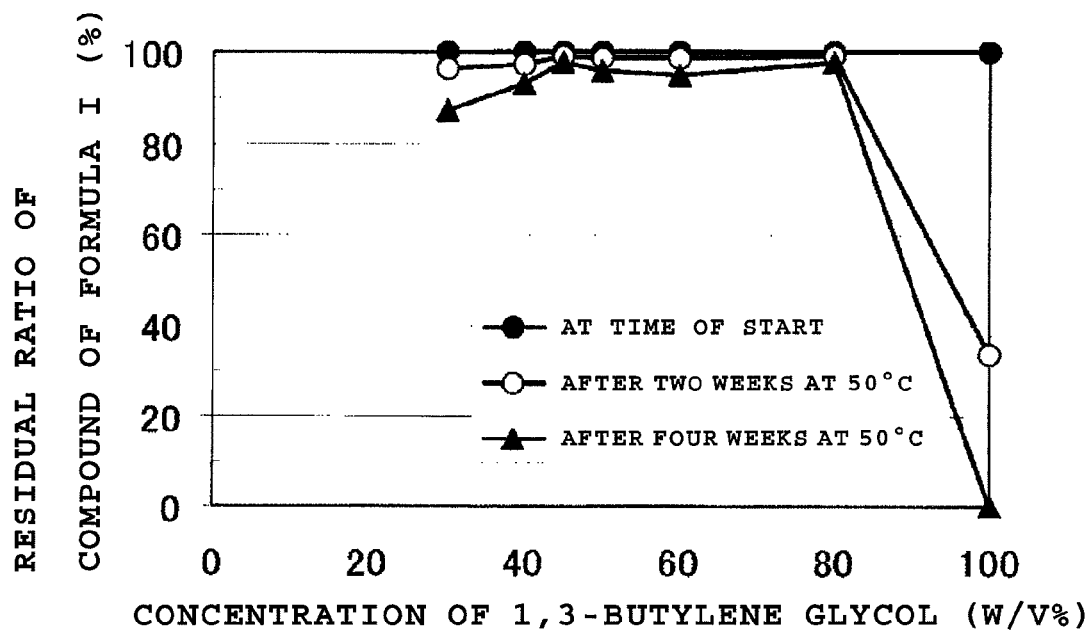
FIG. 1 shows storage stability at 50° C. of lotion preparations containing 0.02 (w/v %) of a compound of formula I with different concentrations of 1,3-butylene glycol.
Figure 2:
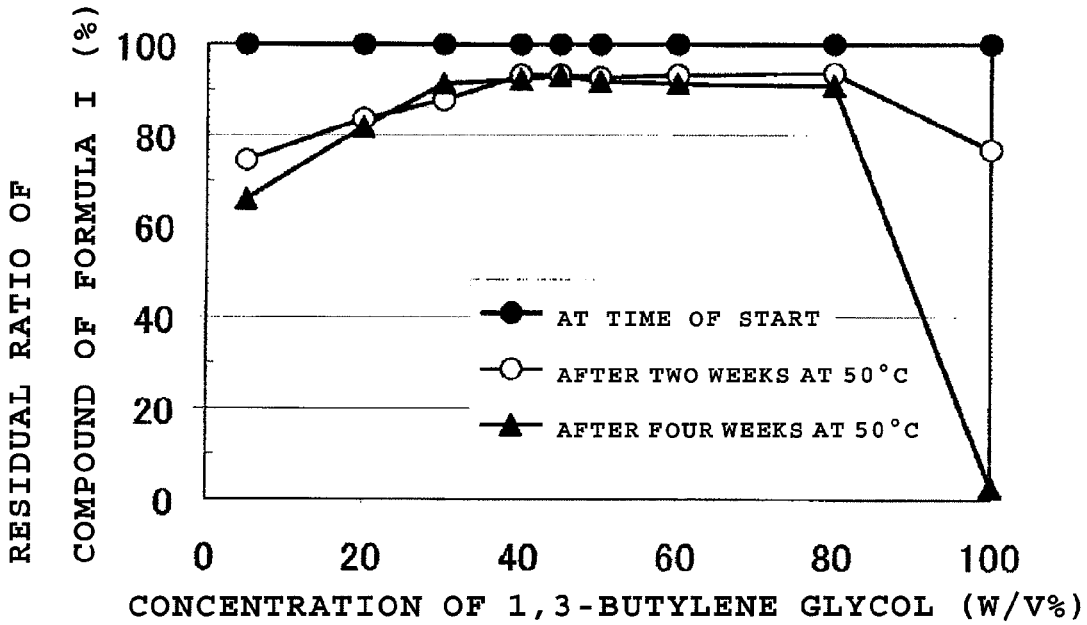
FIG. 2 shows storage stability at 50° C. of lotion preparations containing 0.0001 (w/v %) of the compound of formula I with different concentrations of 1,3-butylene glycol.

The invention claimed is:

1. An aqueous liquid preparation comprising:
   (a) any one of a prostaglandin derivative represented by the following formula (I) and a pharmaceutically acceptable salt thereof:

[Chemical formula 1]

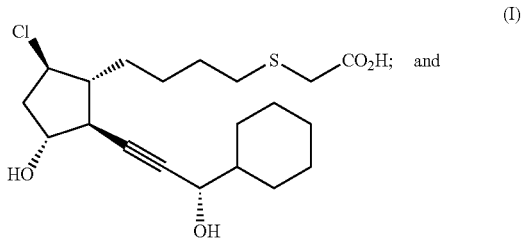

(I)

(b) 1,3-butylene glycol, wherein
   the one of the prostaglandin derivative represented by the formula (I), the pharmaceutically acceptable salt thereof, which is the component (a), is 0.0001 to 0.02 (w/v %) of the total of the aqueous liquid preparation, and
   a content of 1,3-butylene glycol, which is the component (b), is 30 to 80(w/v %) of the total of the aqueous liquid preparation.

2. The aqueous liquid preparation according to claim 1, wherein the aqueous liquid preparation has a pH of 4 to 9.

3. The aqueous liquid preparation according to any one of claims 1 and 2, wherein the aqueous liquid preparation is a lotion.

* * * * *